United States Patent [19]
Haruta et al.

[11] Patent Number: 5,506,273
[45] Date of Patent: Apr. 9, 1996

[54] CATALYST FOR HYDROGENATION AND METHOD FOR HYDROGENATION THEREWITH

[75] Inventors: Masatake Haruta, Ikeda; Hiroaki Sakurai, Osaka; Tetsuhiko Kobayashi; Susumu Tsubota, both of Ikeda; Atsushi Ueda; Masanori Ando, both of Nishinomiya, all of Japan

[73] Assignees: Agency of Industrial Science and Technology; Ministry of International Trade and Industry, both of Tokyo, Japan

[21] Appl. No.: 263,234

[22] Filed: Jun. 21, 1994

Related U.S. Application Data

[60] Continuation-in-part of Ser. No. 59,317, May 11, 1993, abandoned, which is a division of Ser. No. 950,125, Sep. 24, 1992, abandoned.

[30] Foreign Application Priority Data

Dec. 6, 1991 [JP] Japan .................................. 3-349706

[51] Int. Cl.$^6$ .................................................. C07C 27/06
[52] U.S. Cl. .......................... 518/713; 502/344; 502/244
[58] Field of Search ........................... 502/344, 243, 502/244, 245; 518/703, 713, 715

[56] References Cited

U.S. PATENT DOCUMENTS

| | | | |
|---|---|---|---|
| 4,390,639 | 6/1983 | Pesa et al. | 518/713 |
| 4,636,834 | 3/1984 | Wright | 502/201 |
| 4,698,324 | 10/1987 | Haruta et al. | |
| 4,839,327 | 6/1989 | Haruta et al. | |
| 4,937,219 | 6/1990 | Haruta et al. | |
| 5,051,394 | 9/1991 | Haruta et al. | |

OTHER PUBLICATIONS

Patent Abstracts of Japan C-303, Sep. 13, 1985, vol. 9/No. 228.

*Primary Examiner*—Asok Pal
*Assistant Examiner*—Bekir L. Yildirim
*Attorney, Agent, or Firm*—Oblon, Spivak, McClelland, Maier & Neustadt

[57] ABSTRACT

A catalyst for the hydrogenation of CO and $CO_2$ consists essentially of a metal oxide and gold. Synthesis of methanol and hydrocarbons by hydrogenation of CO and $CO_2$ comprises establishing contact between a gaseous mass consisting of CO, $CO_2$, and hydrogen and a catalyst consisting essentially of a metal oxide and gold.

16 Claims, 3 Drawing Sheets

CATALYST FOR HYDROGENATION AND METHOD FOR HYDROGENATION THEREWITH

CROSS-REFERENCE TO RELATED APPLICATION

This application is a continuation in part of application Ser. No. 08/059,317 filed May 11, 1993, now abandoned, which was a division of application Ser. No. 07/950,125 filed Sep. 24, 1992, now abandoned.

BACKGROUND OF THE INVENTION

1. Field of the Invention

This invention relates to a catalyst for the hydrogenation of carbon monoxide or carbon dioxide to be used in synthesizing methanol and/or hydrocarbons by the reaction of carbon monoxide or carbon dioxide with hydrogen and to a method for the synthesis of methanol and/or hydrocarbons by hydrogenation using the catalyst.

2. Prior Art Statement

Being easy to transport and useful in various applications, methanol has become a basic substance in the chemical industry. Commercially, it is synthesized by the reaction of carbon monoxide (CO) with hydrogen. As a catalyst for this reaction, wide use is made of the catalyst (Cu/ZnO) produced by immobilizing copper (Cu) as an active metal on zinc oxide (ZnO). In the actual commercial process for the production of methanol, a $Cu/ZnO/Al_2O_3$ catalyst or a $Cu/ZnO/Cr_2O_3$ catalyst, each incorporating a third component, is additionally used. Though these catalysts exhibit high activity and excel in selectivity, they require reaction temperatures falling in the range between 200° C. and 300° C. under reaction pressures in the range between 50 and 100 atmospheres ($5\times10^6$ and $1\times 10^7$ Pa).

In recent years, the reaction for synthesizing methanol as a useful substance by the combination of carbon dioxide with hydrogen has become the subject intensive laboratory research aimed at enabling effective utilization of carbon dioxide, one of the substances responsible for global warming. Virtually all the catalysts used for the reaction have been those of the Cu/ZnO type. The required reaction conditions include pressures in the range between 50 and 100 atmospheres ($5\times 10^6$ and $1\times10^7$ Pa) and reaction temperatures in the range between 150° C. and 250° C.

It is a characteristic of these reactions for synthesizing methanol by the hydrogenation of carbon monoxide or carbon dioxide that the equilibrium conversion increases with decreasing reaction temperature. In other words, the maximum amount of methanol theoretically obtainable from a given amount of raw materials increases with decreasing reaction temperature. Thus, a strong need has been felt for the development of a catalyst exhibiting high reactivity at the lowest possible temperature.

SUMMARY OF THE INVENTION

In view of this situation, the inventors conducted research for finding a catalyst which exhibits high reactivity at low temperatures in the reaction of hydrogenation of carbon monoxide or carbon dioxide. As a result, they found that a mixture of a metal oxide with gold forms a catalyst which exhibits high reactivity at low temperatures in the hydrogenation of carbon monoxide or carbon dioxide. This invention has been perfected as a result.

Specifically, this invention is directed to a catalyst for the hydrogenation of carbon monoxide or carbon dioxide characterized by comprising a metal oxide and gold and to a method for the production of methanol and/or hydrocarbons characterized by causing a gaseous mass containing carbon monoxide, carbon dioxide, and hydrogen to flow through a bed of the aforesaid catalyst at a temperature of at least 150° C.

DESCRIPTION OF THE PREFERRED EMBODIMENTS

Figure 1:
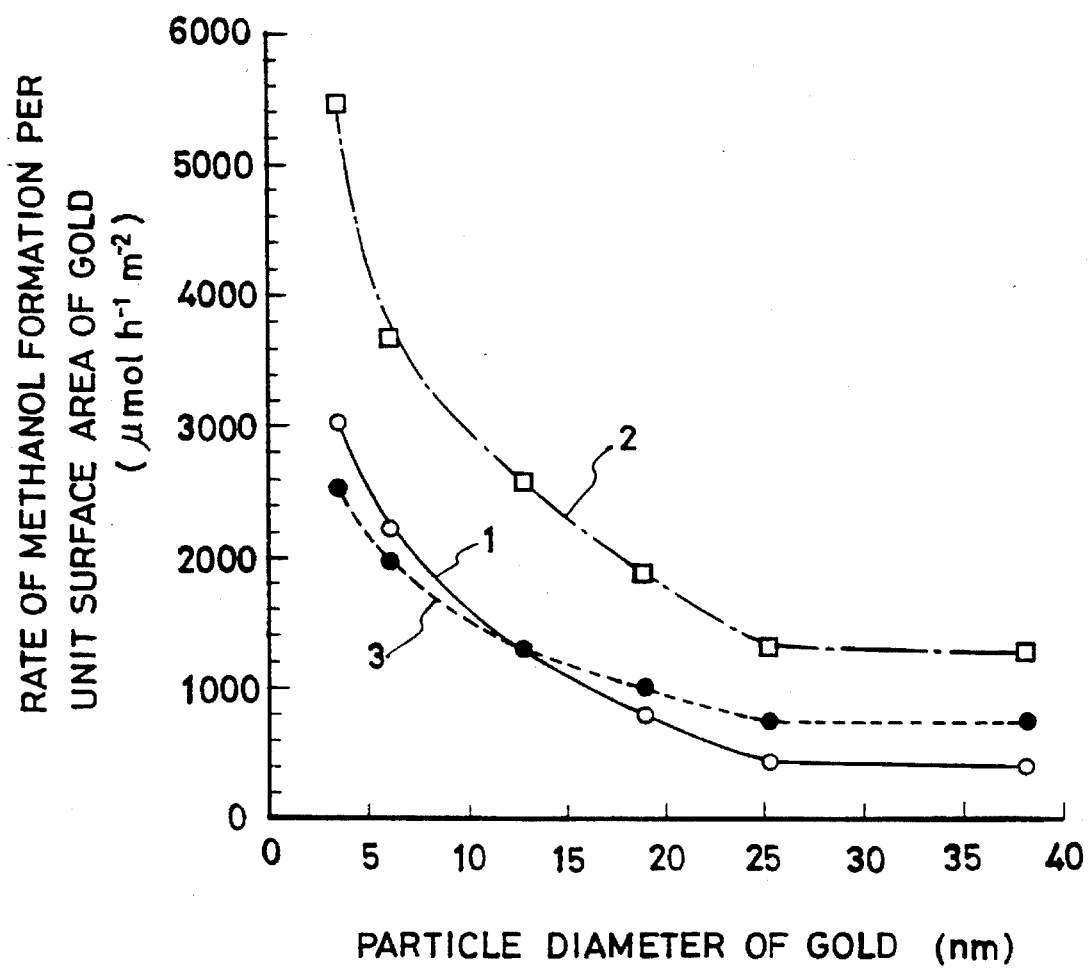
FIG. 1 is a diagram showing the relation between the particle diameter of gold and the rate of methanol formation per unit surface area of gold in Examples 10, 11, and 12.

The catalyst of this invention comprises a metal oxide and gold. The gold is desired to be in the form of minute particles of a diameter of not more than about 0.1 µm, preferably not more than about 10 nm. The form of the metal oxide is not particularly specified. The metal oxide can be used not only in a particulate form but also in a shaped state or as immobilized on any of various substrates.

The metal oxides which can be effectively used in this invention include oxides of single metals such as zinc oxide, iron oxide, copper oxide, lanthanum oxide, titanium dioxide, cobalt oxide, zirconium oxide, magnesium oxide, beryllium oxide, nickel oxide, chromium oxide, scandium oxide, cadmium oxide, indium oxide, tin oxide, manganese oxide, vanadium oxide, cerium oxide, aluminum oxide, and silicon oxide, and complex oxides of elements selected from among zinc, iron, copper, lanthanum, titanium, cobalt, zirconium, magnesium, beryllium, nickel, chromium, scandium, cadmium, indium, tin, manganese, vanadium, cerium, aluminum, and silicon, for example. The single-metal oxides and complex oxides cited above may be used in the form of a mixture of two or more members when necessary. Among the metal oxides listed above, the single oxides or complex oxides of zinc, iron, titanium, zirconium, lanthanum and cerium prove to be particularly desirable.

The catalyst of this invention is particularly desired to be a gold-immobilized metal oxide obtained by immobilizing gold on a metal oxide. The catalyst which has gold immobilized on a metal oxide as described above has a large contact surface area between gold and the metal oxide and is consequently able to manifest an outstanding capacity for catalysts. When gold is immobilized on a metal oxide, the gold is desired to be in the form of minute particles of a diameter of not more than about 0.1 µm, preferably not more than 20 nm, and more preferably not more than 10 nm. When the particle size of the gold used as the catalytic substance is 20 nm or less, the catalytic activity per unit surface area of the gold is remarkably increased. Consequently, the conversion rate of the raw material and the yield of MeOH is remarkably increased.

As reported earlier by the present inventors (Successful Design of Catalysts, pp. 33–42, Elsevier Science Publishers B.V., 1988), gold can be immobilized in the form of particles not more than about 10 nm in diameter on zinc oxide, iron oxide, lanthanum oxide, titanium dioxide, cobalt oxide, zirconium oxide, magnesium oxide, beryllium oxide, nickel oxide, indium oxide, tin oxide, or aluminum oxide. Alternatively, gold can be immobilized in the form of minute particles not more than 0.1 μm in diameter on chromium oxide, cadmium oxide, silicon oxide, copper oxide, scandium oxide, oxide, or manganese oxide. No matter which of the metal oxides mentioned above may be used, the metal oxide not particularly restricted as to the form in which it is used for the immobilization. The metal oxide may be used not only in a particulate form but also in a shaped state or as immobilized on any of various substrates.

Any of various methods well known in the art can used for immobilizing gold on a metal oxide. The methods disclosed in U.S. Pat. Nos. 4,839,327, 4,937,219, and 5,051,394 issued to the present inventors are included among these known methods. As regards the starting materials for these methods, such water-soluble gold compounds as chloroauric acid can be used as a gold source and various nitrates, sulfates, acetates, and chlorides of numerous metals can be used as a metal oxide source. The gold-immobilized metal oxide can be produced as conventionally practiced by the method of coprecipitation which comprises producing a precipitate, separating the precipitate, and drying and calcining the separated precipitate. The calcining temperature may be suitably selected from the range of known calcining conditions. Generally, the calcining temperature which is suitable for the coprecipitation method is in the range between approximately 200° C. and 600° C.

The gold content of the catalyst of this invention can be selected in the range between approximately 0.1 and 30% by weight, based on the total amount of the metal oxide and gold. The reason for this range of the gold content is that at higher gold contents it is difficult to achieve uniform dispersion of the gold and, therefore, the increase in the catalytic activity obtained is not commensurate with the increased amount of gold.

Further, it is permissible from the standpoint of practical utility to use the catalyst of this invention comprising gold and a metal oxide as deposited on a metal oxide carrier prepared in any of various forms. The metal oxide carriers which can be used effectively herein include those made of alumina, silica, cordierite, zeolite, and titanium dioxide, for example. This carrier is not particularly restricted in form. It may be in any of the forms currently in popular use such as, for example, powder spheres, granules, honeycomb, foamed mass, fibers, cloth, plates, and rings. The deposition of the catalyst on the metal oxide carrier can be effected by any of various methods well known to the art. The method disclosed in japanese Unexamined Patent Publication No. 94945/1989, for example, may be adopted.

The catalyst of this invention exhibits activity with respect to the hydrogenation of a gas solely containing carbon monoxide or carbon dioxide and with respect to that of a mixed gas containing both carbon monoxide and carbon dioxide. The hydrogenation of carbon monoxide gives rise to carbon dioxide as a secondary product and the hydrogenation of carbon dioxide produces carbon monoxide as a secondary product. When carbon monoxide or carbon dioxide is hydrogenated, therefore, the gas being produced during the reaction is a mixed gas containing both carbon monoxide and carbon dioxide.

Though the reaction pressure is not particularly critical to the hydrogenation aimed at by this invention, it is desirable to carry out the hydrogenation under a high pressure of not lower than 5 atmospheres ($5 \times 10^5$ Pa) because the selectivity of the hydrogenation for methanol increases in proportion as the reaction pressure increases. Though the optimum reaction temperature is variable with the kind of metal oxide used and other conditions, the catalyst of this invention equals or excels the conventional hydrogenation catalyst in reactivity in the hydrogenation of carbon monoxide and/or carbon dioxide performed under low-temperature conditions of 150° C. to 250° C. Further, by suitably selecting the kind of metal oxide, reaction temperature, etc., methanol or a hydrocarbon can be produced with a high selectivity.

Though the mixing ratio of the raw material gases is not particularly specified, the mixing ratio of $H_2/CO$ in the hydrogenation of carbon monoxide is desired to be 2 or more and the ratio of $H_2/CO_2$ in the hydrogenation of carbon dioxide to be 3 or more by volume. The practical upper limit to these mixing ratios is 10.

In accordance with this invention, a catalyst which exhibits activity with respect to the reaction for synthesis of methanol and/or hydrocarbon by the hydrogenation of carbon monoxide and/or carbon dioxide can be produced. The methanol which is obtained by using the catalyst of this invention is useful as a raw material for such chemicals as formaldehyde, acetic acid, and methyl-t-butyl ether. Moreover, like a hydrocarbon, the methanol can be used as a fuel for various purposes. In addition, the invention enables effective utilization of carbon dioxide arising from industrial activities and, by providing an efficient way for reacting carbon dioxide with hydrogen to obtain methanol, opens the way to the establishment of a system for transporting the energy of hydrogen in the form of markedly easier to transport methanol.

Now, the characteristic features of this invention will be illustrated more specifically below with reference to working examples and comparative experiments.

EXAMPLE 1

In 300 ml of distilled water, 0.003 mol of chloroauric acid [$HAuCl_4 \cdot 4H_2O$] and 0.057 mol of zinc nitrate [$Zn(NO_3)_2 \cdot 6H_2O$] were dissolved (A solution). Separately, 0.101 mol of sodium carbonate [$Na_2CO_3$] was dissolved in 200 ml of distilled water (B solution).

Then, A solution was added dropwise to B solution and the result was stirred for one hour. The coprecipitate which consequently occurred in the mixture was thoroughly washed with water, dried, and calcined in the open air at 400° C. for four hours, to obtain a gold-immobilized zinc oxide catalyst [Au/ZnO, atomic ratio of Au/Zn=1/19]. The catalyst thus produced was tested for ability to promote hydrogenation of carbon monoxide (CO) as follows.

The catalyst was screened to separate a portion of 16 to 42 mesh. One ml (0.59 g) of the separated portion was packed into a bed. A raw material gas (a mixed gas consisting of 33.3% of CO and 66.6% of $H_2$ by volume) was caused to flow through the bed of packed catalyst at a low volume of 50 ml/min. per g of the catalyst under a reaction pressure of 8 atmospheres ($8 \times 10^5$ Pa) to determine the catalyst's ability to catalyze the hydrogenation of CO. The results of this test are shown in Table 1. Table 1 shows conversion of carbon monoxide as a raw material and yields of methanol (MeOH) and hydrocarbon (HC), with the yields of component hydrocarbons of varying numbers of carbons enclosed in the parentheses. The reaction in this case gave rise to carbon dioxide ($CO_2$) as a by-product.

TABLE 1

| Reaction temperature (°C.) | Conversion (%) | Yield of product (%) | | | | | |
|---|---|---|---|---|---|---|---|
| | | MeOH | HC | (CH$_4$ | C2 | C$_3$) | CO$_2$ |
| 150 | 0.0 | 0.0 | 0.0 | (0.0 | 0.0 | 0.0) | 0.0 |
| 200 | 0.0 | 0.0 | 0.0 | (0.0 | 0.0 | 0.0) | 0.0 |
| 250 | 3.9 | 0.4 | 2.0 | (0.9 | 0.6 | 0.5) | 1.5 |
| 300 | 24.6 | 1.5 | 9.9 | (6.0 | 2.7 | 1.2) | 13.2 |
| 350 | 35.6 | 1.7 | 13.2 | (9.9 | 3.3 | 0.0) | 20.7 |
| 400 | 10.6 | 0.1 | 3.8 | (3.4 | 0.4 | 0.0) | 6.7 |

COMPARATIVE EXPERIMENT 1

In 300 ml of distilled water, 0.018 mol of copper nitrate [Cu(NO$_3$)$_2$3H$_2$O] and 0.042 mol of zinc nitrate [Zn(NO$_3$)$_2$.6H$_2$O] were dissolved (A solution). Separately, 0.101 mol of sodium carbonate [Na$_2$CO$_3$] was dissolved in 200 ml of distilled water (B solution).

Then, A solution was added dropwise to B solution and the result was stirred for one hour. The coprecipitate which consequently occurred was thoroughly washed with water, dried, and calcined in the open air at 400° C. for four hours to produce a copper-immobilized zinc oxide catalyst [Cu/ZnO, atomic ratio of Cu/Zn=3/7]. By following the procedure of Example 1, this catalyst was tested for ability to catalyze the hydrogenation of CO. The results are shown in Table 2.

TABLE 2

| Reaction temperature (°C.) | Conversion (%) | Yield of product (%) | | | | | |
|---|---|---|---|---|---|---|---|
| | | MeOH | HC | (CH$_4$ | C2 | C$_3$) | CO$_2$ |
| 150 | 0.3 | 0.0 | 0.0 | (0.0 | 0.0 | 0.0) | 0.3 |
| 200 | 0.3 | 0.0 | 0.0 | (0.1 | 0.0 | 0.0) | 0.3 |
| 250 | 4.0 | 0.5 | 1.5 | (1.1 | 0.4 | 0.0) | 2.0 |
| 300 | 16.1 | 1.2 | 5.5 | (3.7 | 1.8 | 0.0) | 9.4 |
| 350 | 41.0 | 1.8 | 16.6 | (12.1 | 4.5 | 0.0) | 22.6 |
| 400 | 42.0 | 1.2 | 18.5 | (14.1 | 4.5 | 0.0) | 22.3 |

The Au/ZnO catalyst and the Cu/ZnO catalyst both aided in producing methanol and hydrocarbons at temperatures exceeding 250° C. A comparison of the results in Table 1 and Table 2 clearly indicates that the Au/ZnO catalyst manifested improved activity in a relatively low temperature range of 250° C. to 350° C. as compared with the conventional Cu/ZnO catalyst.

EXAMPLE 2

The Au/ZnO catalyst obtained in Example 1 was tested for activity in the hydrogenation of CO$_2$ as follows.

The catalyst was screened to separate a portion of 16 to 42 mesh and 1 ml (0.59 g) of the separated portion was packed into a bed. A raw material gas (a mixed gas consisting of 23.4% of CO$_2$, 66.2% of H$_2$, and 10.4% of Ar Dy volume) was caused to flow through the bed of the packed catalyst at a flow volume of 50 ml/min per g of the catalyst under a reaction pressure of 8 atmospheres (8×10$^5$ Pa) to determine the catalyst's activity in the reaction of hydrogenation of CO$_2$. The results of this reaction are shown in Table 3.

EXAMPLE 3

A Au/Fe$_2$O$_3$ catalyst was prepared by following the procedure of Example 1 and tested for catalytic activity by following the procedure of Example 2. The results are shown in Table 3.

EXAMPLE 4

In 1,000 ml of distilled water, 0.002 mol of chloroauric acid [HAuCl$_4$.4H$_2$O] was dissolved. The resultant solution was adjusted to a pH value in the range between 7 and 10 by dropwise addition thereto of an aqueous 1 mol/liter NaOH solution. The solution and 3.0 g of titanium dioxide powder added thereto were stirred for one hour. The coprecipitate which consequently occurred was thoroughly washed with distilled water, dried, and calcined in the air at 400° C. for four hours to produce a gold-immobilized titanium dioxide catalyst [Au/TiO$_2$, atomic ratio of Au/Ti=1/19].

The catalyst was tested for catalytic activity by following the procedure of Example 2. The results are shown in Table 3.

EXAMPLE 5

A Au/ZrO$_2$ catalyst was prepared by following the procedure of Example 1 and tested for catalytic activity by following the procedure of Example 2. The results are shown in Table 3.

EXAMPLE 6

A Au/La$_2$O$_3$ catalyst was prepared by following the procedure of Example 1 (except that the calcining temperature was changed to 200° C.) and tested for catalytic activity by following the procedure of Example 2. The results are shown in Table 3.

EXAMPLE 7

In 300 ml of distilled water, 0.003 mol of chloroauric acid [HAuCl$_4$.4H$_2$O], 0.019 mol of zinc nitrate [Zn(NO$_3$)$_2$.6H$_2$O], and 0.038 mol of iron nitrate [Fe(NO$_3$)$_3$.9H$_2$O] were dissolved (A solution). Separately, 0.101 mol of sodium carbonate [Na$_2$CO$_3$] was dissolved in distilled water (B solution).

Then, A solution was added dropwise to B solution and the result was stirred for 15 minutes. The coprecipitate which consequently occurred was thoroughly washed with water, dried, and calcined in the air at 400° C. for four hours to produce a catalyst for hydrogenation [atomic ratio of Au/(Zn+Fe)=1/19]. It was confirmed by X-ray diffraction analysis that this catalyst was composed of zinc ferrite, a composite oxide of zinc and iron, and minute gold particles [Au/ZnFe$_2$O$_4$].

This catalyst was tested for catalytic activity by following the procedure of Example 2. The results are shown in Table 3.

EXAMPLE 8

In 200 ml of an aqueous solution containing iron nitrate [Fe(NO$_3$)$_3$.9H$_2$O] in a concentration of 0.5 mol/liter, 100 g of granular alumina pellets about 3 mm in diameter were left standing for three hours. Then, the wet pellets were heated in a rotary vacuum evaporator to expel moisture. The granular pellets consequently obtained were placed in a tubular container and calcined under a flow of air at 400° C. for five hours, to produce granular alumina pellets having iron oxide deposited thereon. The pellets were immersed in 300 ml of an aqueous potassium carbonate solution having 1.1 g of potassium chloroaurate [KAuCl$_4$.2H$_2$O] dissolved therein and having a pH value of 10, with the aqueous solution kept stirred by means of a circulation pump. To the aqueous solution, 20 ml of an aqueous solution containing formalin in a concentration of 3.7% by weight was gradually added dropwise over a period of 50 minutes, to induce precipitation of gold by reduction. The pellets in the mixed solution were separated by filtration, washed several times, dried, and calcined in the air at 400° C. for four hours, to produce a catalyst of granular iron oxide pellets immobilized 0.5 weight % of gold.

This catalyst was tested for catalytic activity by following the procedure of Example 2. The results are shown in Table 3.

EXAMPLE 9

A $Au/CeO_2$ catalyst was prepared by following the procedure of Example 4 and tested for catalytic activity by following the procedure of Example 2. The results are shown in Table 3.

COMPARATIVE EXPERIMENT 2

A Cu/ZnO catalyst was produced by following the procedure of Example 2 and tested for catalytic activity by following the procedure of Example 2. The results are shown in Table 3.

COMPARATIVE EXPERIMENT 3

A zinc oxide catalyst (ZnO) was tested for catalytic activity by following the procedure of Example 2. The results are shown in Table 3.

COMPARATIVE EXPERIMENT 4

An iron oxide catalyst ($Fe_2O_3$) was tested for catalytic activity by following the procedure of Example 2. The results are shown in Table 3.

TABLE 3

| Catalyst | | Temperature (°C.) | | | | | |
|---|---|---|---|---|---|---|---|
| | | 150 | 200 | 250 | 300 | 350 | 400 |
| Example 2 | Conversion | 0.0 | 0.0 | 2.4 | 8.0 | 21.5 | 35.9 |
| Au/ZnO | Selectivity for MeOH | | | 50.6 | 8.8 | 0.0 | 0.0 |
| | Selectivity for HC | | | 0.0 | 0.0 | 0.0 | 0.0 |
| | Selectivity for CO | | | 49.4 | 91.2 | 100.0 | 100.0 |
| Example 3 | Conversion | 0.9 | 4.1 | 14.7 | 23.6 | 31.6 | 39.2 |
| $Au/Fe_2O_3$ | Selectivity for MeOH | 0.0 | 15.1 | 4.4 | 0.0 | 0.0 | 0.0 |
| | Selectivity for HC | 0.0 | 0.0 | 0.0 | 0.3 | 1.3 | 3.6 |
| | Selectivity for CO | 100.0 | 84.9 | 95.6 | 99.7 | 98.7 | 96.4 |
| Example 4 | Conversion | 3.5 | 9.3 | 16.1 | 23.1 | 30.9 | 39.2 |
| $Au/TiO_2$ | Selectivity for MeOH | 0.0 | 1.0 | 1.0 | 0.2 | 0.0 | 0.0 |
| | Selectivity for HC | 0.0 | 0.0 | 5.3 | 8.6 | 9.2 | 8.7 |
| | Selectivity for CO | 100.0 | 99.0 | 93.7 | 91.2 | 90.8 | 91.3 |
| Example 5 | Conversion | 1.0 | 1.9 | 9.2 | 20.8 | 31.7 | 40.0 |
| $Au/ZrO_2$ | Selectivity for MeOH | 0.0 | 5.2 | 3.3 | 0.0 | 0.0 | 0.0 |
| | Selectivity for HC | 0.0 | 0.0 | 0.0 | 1.4 | 1.0 | 2.3 |
| | Selectivity for CO | 100.0 | 94.8 | 96.7 | 98.6 | 99.0 | 97.7 |
| Example 6 | Conversion | 0.1 | 0.4 | 2.3 | 9.3 | 21.5 | 34.7 |
| $Au/La_2O_3$ | Selectivity for MeOH | 0.0 | 0.0 | 6.5 | 2.4 | 0.0 | 0.0 |
| | Selectivity for HC | 0.0 | 0.0 | 0.0 | 0.0 | 0.0 | 0.0 |
| | Selectivity for CO | 100.0 | 100.0 | 93.5 | 97.6 | 100.0 | 100.0 |
| Example 7 | Conversion | 0.0 | 0.0 | 2.5 | 7.5 | 22.7 | 35.2 |
| $Au/ZnFe_2O_4$ | Selectivity for MeOH | | | 44.0 | 6.7 | 0.0 | 0.0 |
| | Selectivity for HC | | | 0.0 | 1.6 | 10.6 | 8.5 |
| | Selectivity for CO | | | 56.0 | 91.7 | 89.4 | 91.5 |
| Example 8 | Conversion | 0.0 | 3.6 | 13.5 | 20.9 | 31.3 | 37.9 |
| $Au/Fe_2O_3$ | Selectivity for MeOH | | 12.2 | 5.2 | 0.4 | 0.0 | 0.0 |
| (deposited on an | Selectivity for HC | | 0.0 | 0.0 | 1.0 | 1.9 | 4.5 |
| alumina pellets) | Selectivity for CO | | 87.8 | 94.8 | 98.6 | 98.1 | 95.5 |
| Example 9 | Conversion | 0.7 | 1.0 | 3.4 | 8.6 | 18.2 | 36.4 |
| $Au/CeO_2$ | Selectivity for MeOH | 0.0 | 0.0 | 5.2 | 2.7 | 0.0 | 0.0 |
| | Selectivity for HC | 0.0 | 0.0 | 0.0 | 0.0 | 0.0 | 0.0 |
| | Selectivity for CO | 100.0 | 100.0 | 94.8 | 97.3 | 100.0 | 100.0 |
| Comparative | Conversion | 0.3 | 4.6 | 16.0 | 24.0 | 31.0 | 38.9 |
| Experiment 2 | Selectivity for MeOH | 55.0 | 38.3 | 4.6 | 0.6 | 0.2 | 0.0 |
| Cu/ZnO | Selectivity for HC | 0.0 | 0.0 | 0.0 | 0.0 | 0.0 | 0.0 |
| | Selectivity for CO | 45.0 | 61.7 | 95.4 | 99.4 | 99.8 | 100.0 |
| Comparative | Conversion | 0.0 | 0.0 | 0.4 | 1.4 | 4.6 | 13.0 |
| Experiment 3 | Selectivity for MeOH | | | 0.0 | 14.1 | 6.9 | 0.0 |
| ZnO | Selectivity for HC | | | 0.0 | 0.0 | 0.0 | 0.0 |
| | Selectivity for CO | | | 100.0 | 85.9 | 93.1 | 100.0 |
| Comparative | Conversion | 0.0 | 0.0 | 0.2 | 3.1 | 22.6 | 39.3 |
| Experiment 4 | Selectivity for MeOH | | | 0.0 | 2.5 | 0.0 | 0.0 |
| $Fe_2O_3$ | Selectivity for HC | | | 0.0 | 0.0 | 0.0 | 0.0 |
| | Selectivity for CO | | | 100.0 | 97.5 | 100.0 | 100.0 |

EXAMPLE 10

In 1000 ml of distilled water, 0.002 mol of chloroauric acid [$HAuCl_4 \cdot 4CH_2O$] was dissolved. The resultant solution was adjusted to a pH value in the range between 7 and 10 by dropwise addition thereof of an aqueous 1 mol/liter NaOH solution. Powdered zinc oxide calcined at 800° C. was added in the amount of 3.0 g to this resultant solution and stirred for one hour. The coprecipitate which consequently occurred was thoroughly washed with distilled water, dried, and calcined in the air for four hours. The calcining temperature was varied in the range between 400° C. and 750° C. to produce six kinds of gold-immobilized zinc oxide catalysts [Au/ZnO, atomic ratio of Au/Zn=0.007~0.008].

The diameter of gold particles of each catalyst was measured by the electron microscope. Many gold particles were immobilized on the surface of the catalysts. The average diameter of the respective catalysts was measured.

A rate of formation of methanol per unit surface area of gold for each catalyst was measured under the following condition. A raw material (a mixed gas consisting of 23.0% of $CO_2$, 67.0% of $H_2$ and 10.0% of Ar by volume) was passed through each catalyst under a pressure of 50 atmospheres ($50 \times 10^5$ Pa), at a rate of flow of 50 ml/min per g of each catalyst and at a temperature of 250° C.

The rate of formation of methanol per unit surface area of gold in the above condition is shown by curve 1 in FIG. 1. The products were methanol and CO.

EXAMPLE 11

The same procedure as in Example 10 were carried out except that the temperature at which the raw material was passed through the catalyst was changed to 300° C. The result was shown by curve 2 in FIG. 1. The products were methanol and CO.

EXAMPLE 12

The same procedures as in the Example 10 were carried out except that a mixed gas consisting of 30.0% of CO, 60% of $H_2$ and 10% of Ar by volume was used as the raw material. The result is shown by curve 3 in FIG. 1. The products were methanol.

EXAMPLE 13

The average diameter of gold particles of five kinds of gold-immobilized titanium oxide catalysts [$Au/TiO_2$, atomic ratio of Au/Ti=0.012–0.014] obtained by the same reaction as that of Example 10 (except that titanium oxide was used instead of zinc oxide) was measured in the same manner as in Example 10 (except that titanium oxide was used instead of zinc oxide). The rate of formation of methanol per unit surface area of gold for each catalyst was measured under the following condition.

A raw material (a mixed gas consisting of 23.0% of $CO_2$, 67.0% of $H_2$ and 10.0% of Ar by volume) was passed through each catalyst under a pressure of 50 atmospheres ($50 \times 10^5$ Pa), at a rate of flow of 50ml/min per g of each catalyst and at a temperature of 220° C.

Figure 2:
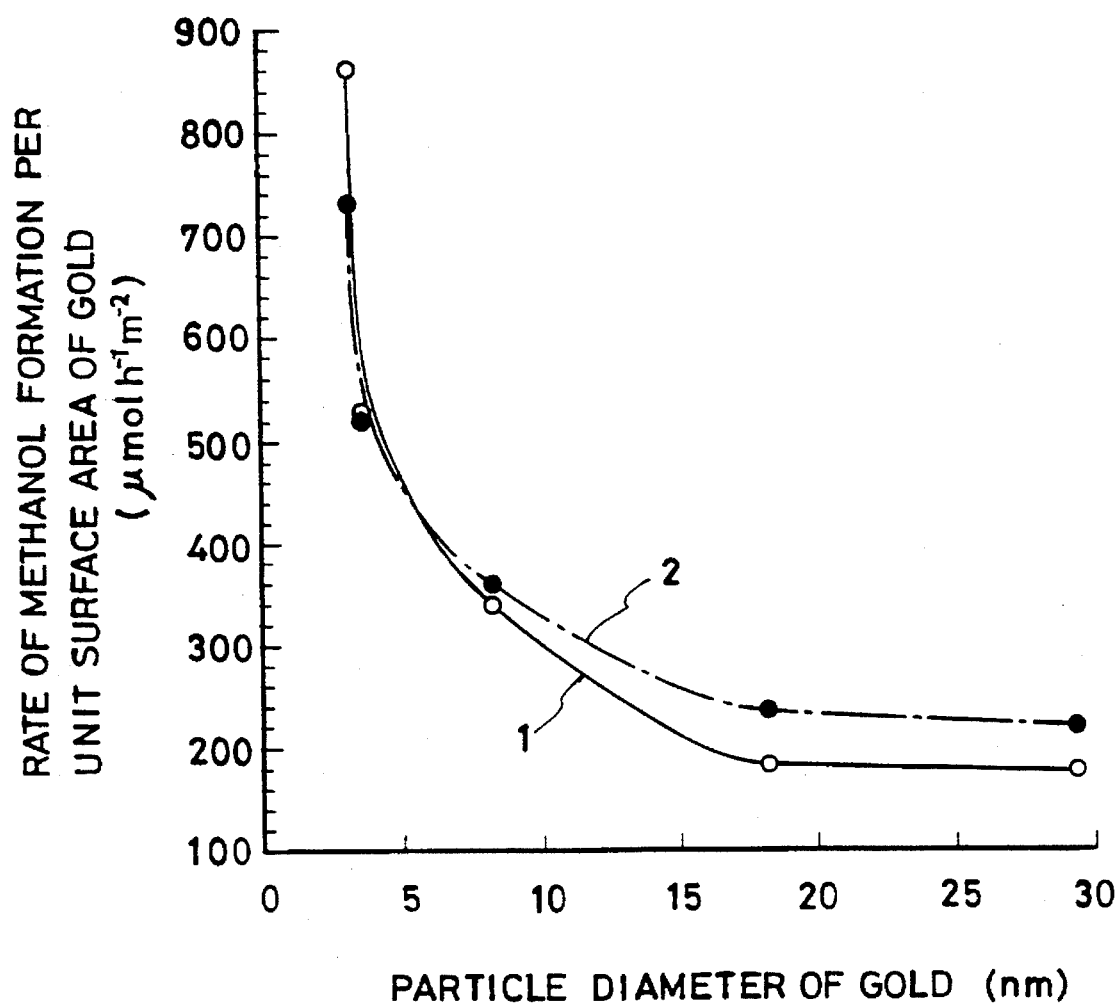
FIG. 2 is a diagram showing the same relation in Examples 13 and 14.

The rate of formation of methanol per unit surface area of gold in the above condition is shown in curve 1 in FIG. 2. The products were methanol and CO.

EXAMPLE 14

The same procedures as in Example 13 were carried out except that a mixed gas consisting of 30.0% of CO, 60% of $H_2$ and 10.0% of Ar by volume was used as the raw material. The result is shown by curve 2 in FIG. 2. The products was methanol.

EXAMPLE 15

The average diameter of gold particles of six kinds of gold-immobilized oxide iron catalyst [$Au/Fe_2O_3$, atomic ratio of Au/Fe=0.009–0.012] obtained by the same reaction as that of Example 12 (except that iron oxide was used instead of zinc oxide) was measured in the same manner as that used in added Example 1. The rate of formation of methanol per unit surface area of gold for each catalyst was measured by the following condition.

Figure 3:
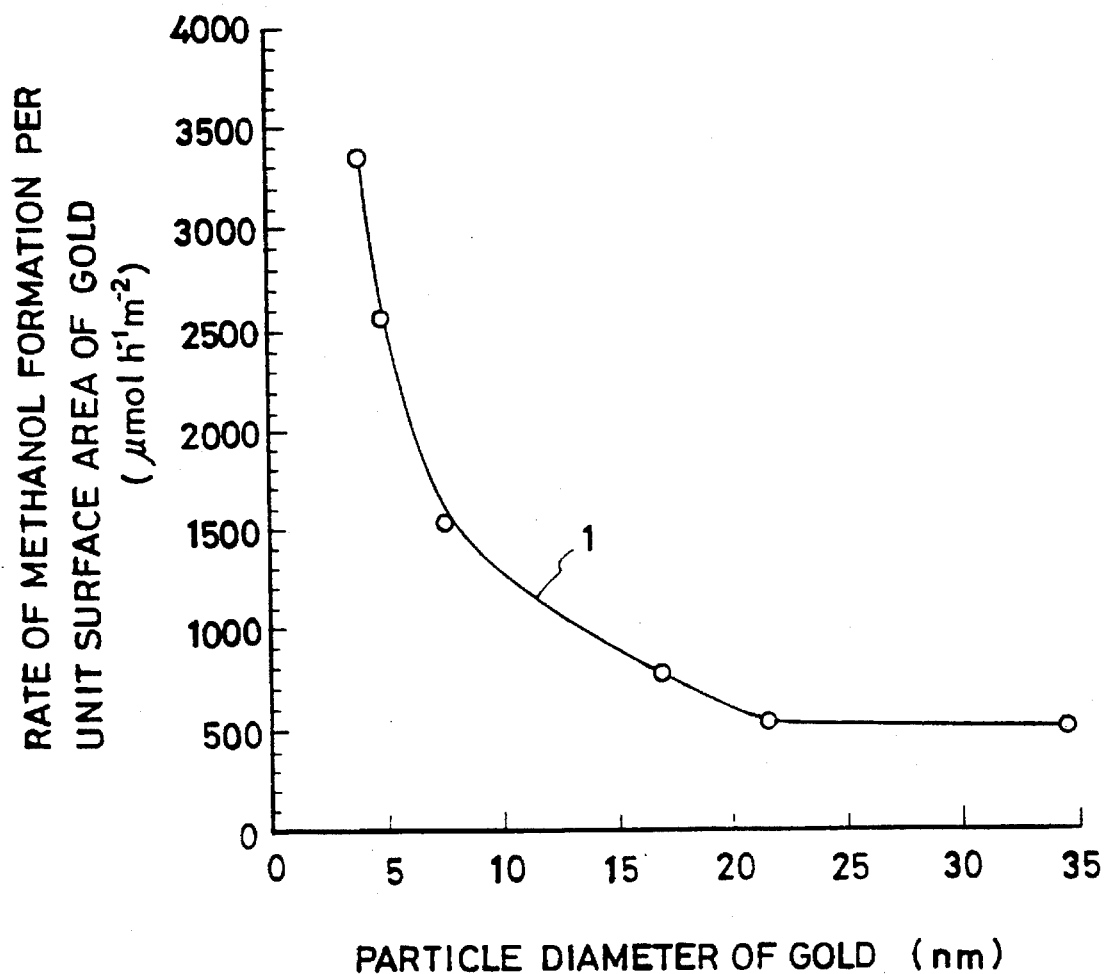
FIG. 3 is a diagram showing the same relation in Example 15.

A raw material (a mixed gas consisting of 23.0% of $CO_2$, 67.0% of $H_2$ and 10.0% of Ar by volume) was passed through each catalyst under a pressure of 50 atmospheres ($50 \times 10^5$ Pa), at a rate of flow 50 ml/min per 1 g of catalyst and at a temperature of 250° C. The rate of formation of methanol per unit surface area of gold in the above condition is shown by curve 1 in FIG. 3. The products were methanol and CO.

These results clearly indicate that the catalysts of the present invention have the following characteristics.

(1) They equal or excel the $Au/Fe_2O_3$, $Au/TiO_2$, and Cu/ZnO catalysts in conversion and excel them in activity at low temperatures in the range between 150° C. and 200° C.

(2) At 200° C. to 250° C., the temperature range in which the Cu/ZnO catalyst functions most efficiently in the formation of methanol, the catalysts of this invention invariably exhibit ability to synthesize methanol.

(3) The Au/ZnO catalyst, though liable to lose selectivity for methanol in proportion as the reaction temperature increases, excels in selectivity, as evidenced by the fact that the selectivity for methanol is 50% at 250° C.

(4) $Au/Fe_2O_3$, $Au/TiO_2$, and $Au/ZnFe_2O_4$ catalysts aid in producing hydrocarbons (mostly methane, except that the first and third catalysts produce ethane and propane in small amounts).

(5) The gold-immobilized catalysts (Au/ZnO and $Au/Fe_2O_3$) are capable of synthesizing methanol at lower temperatures than the catalysts formed solely of an oxide (ZnO and $Fe_2O_3$).

(6) The gold used as a catalytic substance should be in the form of minute particles of a diameter not more than about 0.1 μm. When the particle size of the gold is at the lower end of the range, preferably 20 nm or less, the catalytic activity per unit surface area of the gold is remarkably increased.

What is claimed is:

1. A method for the hydrogenation of at least one carbon oxide selected from the group consisting of CO and $CO_2$, which comprises preparing a gaseous mass containing said at least one carbon oxide and hydrogen and feeding said gaseous mass into contact with a catalyst essentially consisting of a metal oxide and gold at a temperature of between 150° C. and 400° C., said gold having a particle size of less than 20 nm.

2. A method according to claim 1, wherein the metal forming said metal oxide is at least one member selected from the group consisting of zinc, iron, copper, lanthanum, titanium, cobalt, zirconium, magnesium, beryllium, nickel, chromium, scandium, cadmium, indium, tin, manganese, vanadium, cerium, aluminum, and silicon.

3. A method according to claim 2, wherein the metal forming said metal oxide is at least one member selected from among zinc, iron, titanium, zirconium, lanthanum and cerium.

4. A method for the synthesis of methanol by the hydrogenation of at least one carbon oxide selected from the group consisting of CO and $CO_2$, comprising; preparing a gaseous mass containing said at least one carbon oxide and hydrogen and feeding said gaseous mass into contact with a catalyst consisting essentially of a metal oxide and gold at a temperature of between 150° C. and 400° C., said gold having a particle size of less than 20 nm.

5. A method according to claim 4, wherein the reaction pressure is at least $5\times10^5$ Pa.

6. A method according to claim 4, wherein said carbon oxide is CO and the volumetric ratio of $H_2/CO$ is at least 2.

7. A method according to claim 4, wherein said carbon oxide is $CO_2$ and the volumetric ratio of $H_2/CO_2$ is at least 3.

8. A method according to claim 4, wherein the gold content is in the range between 0.1 and 30% by weight, based on the total amount of said metal oxide and gold.

9. A method according to claim 4, wherein said gold is in the form of minute particles not more than about 10 nm in maximum diameter.

10. A method according to claim 4, wherein said gold is immobilized on said metal oxide.

11. A method according to claim 4, wherein the catalyst is deposited on a carrier.

12. A method according to claim 11, wherein said carrier is formed of at least one member selected from the group consisting of alumina, silica, zeolite, and titanium dioxide.

13. A method for producing with high yield a mixture consisting essentially of CO and methanol, comprising the step of bringing a gaseous mass containing hydrogen and at least one carbon oxide selected from the group consisting of CO and $CO_2$ into contact with a catalyst consisting essentially of gold in the form of minute particles less than 20 nm in diameter and at least one oxide of zinc, iron, titanium, zirconium, lanthanum or cerium, at a temperature between about 200° C. and about 350° C. under a reaction pressure of not less than $5\times10^5$ Pa.

14. The method of claim 13, wherein the particle size of the gold used as a catalytic substance is not more than 10 nm.

15. A method for the hydrogenation of at least one carbon oxide selected from the group consisting of CO and $CO_2$, which comprises preparing a gaseous mass containing said at least one carbon oxide and hydrogen and feeding said gaseous mass into contact with a catalyst consisting essentially of a metal oxide and gold, at a temperature of between 150° C. and 400° C., said gold having a particle size of less than 20 nm.

16. The process of claim 15, wherein said gold has a particle size of not more than about 10 nm.

* * * * *

UNITED STATES PATENT AND TRADEMARK OFFICE
CERTIFICATE OF CORRECTION

PATENT NO. : 5,506,273
DATED : April 9, 1996
INVENTOR(S) : Masatake HARUTA, et al.

It is certified that error appears in the above-indentified patent and that said Letters Patent is hereby corrected as shown below:

On the title page, Item [73], the assignee, should read:

--Agency of Industrial Science and Technology,
Ministry of International Trade and Industry,
of Tokyo, Japan--

Signed and Sealed this

Sixth Day of August, 1996

*Attest:*

BRUCE LEHMAN

*Attesting Officer*   Commissioner of Patents and Trademarks